US010013870B2

(12) United States Patent
Treccani

(10) Patent No.: US 10,013,870 B2
(45) Date of Patent: Jul. 3, 2018

(54) ACTIVATION METHOD OF AN ALARM FOR RISK OF AGGRESSION TO A USER AND A DEVICE IMPLEMENTING SAID METHOD

(71) Applicant: Dares Technologies S.R.L., Collebeato (IT)

(72) Inventor: Daniele Treccani, Leno (IT)

(73) Assignee: DARES TECHNOLOGIES S.R.L., Collebeato (BS) (IT)

( * ) Notice: Subject to any disclaimer, the term of this patent is extended or adjusted under 35 U.S.C. 154(b) by 29 days.

(21) Appl. No.: 15/111,284

(22) PCT Filed: Jan. 27, 2015

(86) PCT No.: PCT/IB2015/050597
§ 371 (c)(1),
(2) Date: Jul. 13, 2016

(87) PCT Pub. No.: WO2015/114510
PCT Pub. Date: Aug. 6, 2015

(65) Prior Publication Data
US 2016/0335880 A1    Nov. 17, 2016

(30) Foreign Application Priority Data

Jan. 28, 2014 (IT) .............................. BS2014A0028

(51) Int. Cl.
*G08B 1/08* (2006.01)
*G08B 25/01* (2006.01)
(Continued)

(52) U.S. Cl.
CPC ............ *G08B 25/016* (2013.01); *A61B 5/024* (2013.01); *A61B 5/02438* (2013.01);
(Continued)

(58) Field of Classification Search
CPC ... A61B 5/024; A61B 5/02438; A61B 5/0464; A61B 5/681; A61B 5/746; G08B 21/0297; G08B 25/001; G08B 25/016; G08B 29/24
(Continued)

(56) References Cited

U.S. PATENT DOCUMENTS 5,607,460 A * 3/1997 Kroll .................... G16H 50/20
607/30
6,609,023 B1 * 8/2003 Fischell ............... A61B 5/0031
600/515
(Continued)

FOREIGN PATENT DOCUMENTS

CN    103456132 A    12/2013
DE    10139749 A1    2/2003
(Continued)

OTHER PUBLICATIONS

International Search Report for International Application No. PCT/IB2015/050597(dated May 29, 2015)(3 Pages).

*Primary Examiner* — Naomi J Small
(74) *Attorney, Agent, or Firm* — Lucas & Mercanti, LLP

(57) ABSTRACT

An alarm method for risk of aggression to a user is disclosed. The method includes collecting information on the user's heart reaction to physical efforts; collecting information on the level of bradycardia or tachycardia of the user; determining reference values relating to the user's heart rate beyond which the alarm has to be activated, measuring parameters relating to the user's heart rate; and activating the alarm every time the measured parameters exceed the reference values. A portable alarm device implementing the method includes: a heart rate meter; a control unit; a memory circuit; a program computer product executed by the control unit in order to collect the information on the user and (Continued)

determine the reference values relating to the user's heart rate beyond which the alarm has to be activated; and alarm means for the rescue request.

26 Claims, 1 Drawing Sheet

(51) Int. Cl.
    *G08B 21/02*     (2006.01)
    *G08B 29/24*     (2006.01)
    *A61B 5/00*     (2006.01)
    *A61B 5/024*     (2006.01)
    *A61B 5/0464*     (2006.01)
    *G08B 25/00*     (2006.01)

(52) U.S. Cl.
    CPC ............ *A61B 5/0464* (2013.01); *A61B 5/681* (2013.01); *A61B 5/746* (2013.01); *G08B 21/0297* (2013.01); *G08B 29/24* (2013.01); *G08B 25/001* (2013.01)

(58) Field of Classification Search
    USPC ..................................................... 340/539.12
    See application file for complete search history.

(56) References Cited

U.S. PATENT DOCUMENTS

| | | | | |
|---|---|---|---|---|
| 2008/0204558 A1* | 8/2008 | Goldman | ............. | A61B 5/0006 348/153 |
| 2008/0266118 A1* | 10/2008 | Pierson | ................ | A61B 5/0205 340/573.6 |
| 2010/0132100 A1* | 6/2010 | Courtney | ............. | A62B 17/006 2/457 |
| 2010/0274147 A1* | 10/2010 | Patangay | ................ | A61B 5/024 600/515 |
| 2013/0231947 A1* | 9/2013 | Shusterman | ........ | G06F 19/3418 705/2 |
| 2014/0232885 A1* | 8/2014 | Slater | ..................... | H04N 5/232 348/207.11 |

FOREIGN PATENT DOCUMENTS

| | | |
|---|---|---|
| WO | 2004078028 A2 | 9/2004 |
| WO | 2006119345 A2 | 11/2006 |
| WO | 2010092192 A1 | 8/2010 |

* cited by examiner

ACTIVATION METHOD OF AN ALARM FOR RISK OF AGGRESSION TO A USER AND A DEVICE IMPLEMENTING SAID METHOD

CROSS-REFERENCE TO RELATED APPLICATIONS

This application is a 371 of PCT/IB2015/050597, filed Jan. 27, 2015 which claims the benefit of Italian Patent Application No. BS2014A000028 filed Jan. 28, 2014.

TECHNICAL FIELD

The present invention can be applied to the security and rescue field and, in particular, it concerns the field of devices for personal security.

More in detail, the present invention refers to the field of portable devices the persons use for rescue request.

STATE OF THE ART

As the years go by, the personal security became a problem the population felt increasingly. More and more often, through the media, we know about mugging and robberies to persons during their displacements from a place to another.

The easier solution for the use is to be provided with a mobile phone through which the user could make a rescue request call. However, the user not always has the way and the time to make a call. Furthermore, frequently the user is not able to provide immediate information on the place where he/she is.

Therefore, during last years a plurality of devices has been developed through which the users send a rescue request signal when in a danger condition.

These devices, when operated, activate a rescue request signal through a circuit transceiving radio-frequency signals. Usually it all comes down to an automatic voice or date call to security forces, health care professionals, conveniently organized rescue services, or similar. In detail, when such devices are activated they take care to detect their own position in order to provide such an information to the rescue personnel.

However, also in this case the device can fail since the user could not even have the time to activate it.

Therefore, device are known that are automatically activated on the basis of signals coming from accelerometers detecting user's violent displacements or ground falls, or on the basis of possible damages to the device itself. However, such situations can provide false alarms (the user could simply stumble) or failed alarms if the user is immobilized without struggling (usually under gunpoint).

Document US 2008/204558 describes a security system for a facility, for example a bank, comprising a central monitoring station that controls one or more security measures for the facility; and a heart rate monitor that detects the heart rate of an individual, the heart rate monitor being in wireless communication with the central monitoring station and the central monitoring station selectively implementing one or more of the security measures in response to a determination that an abnormal heart rate has been detected.

Document WO 2004/078028 describes jewelry, such as finger rings or earrings, having a system for detecting the heartbeat of a user and at least one light emitting source flashing in synchronism with the wearer's heartbeat.

Document WO 2010/092192 describes a personal attack alarm adapted to be activated by a user, when the user wishes to summon help, comprising: a portable unit the user can wear and apt to transmit an alarm signal to a receiver of the alarm signal; wherein the signal is transmitted by means of a telecommunications network when the user activates the alarm by urinating, and wherein the portable unit comprises a wetness sensor and a transmitter.

SUMMARY OF THE INVENTION

An object of the present invention is to overcome, at least partially, the afore mentioned drawbacks by providing an activation method of an alarm for risk of aggression to a user and a device implementing such a method which are automatically activated.

Another object of the present invention is that the method and the device implementing it, allow limiting, if not canceling, false alarms.

Another object of the present invention is that the method, and the device implementing it, allow limiting, if not canceling, alarm situations that are not reported because not detected.

Such objects, as others that will become more evident in the following, are achieved by an activation method of an alarm for risk of aggression to a user according to one or more of the attached claims, which are integral part of the present patent.

In particular, the method comprises a step of collecting information on the user's heart reaction to physical efforts and a step of collecting information on the level of bradycardia or tachycardia of the user.

Advantageously, these steps allow deducing the user's physical condition. Then there is a step in which one or more reference values are determined, which relate to the user's heart rate beyond which the alarm has to be activated. In particular, these one or more reference values are determined on the basis of the collected information on the heart reaction to physical efforts and/or on the level of bradycardia or tachycardia.

After the afore said steps, there are a step of measuring one or more parameters relating to the user's heart rate and a step of activating the alarm every time one or more measured parameters exceed the previously determined reference values.

In other terms, the method object of the present invention determines some threshold values of heart parameters such as, for example, the heart rate and the variations of heart rate that, when they are reached or exceeded, are responsive to high stress and anxiety situations typically due to mugging or similar events. As a matter of fact, it is known that such threshold or reference values are surely higher than heart rate values, or variations of heart rate, due to physical efforts or other situations normally happening during the day.

Typically, these reference values can be determined by referring to a reference value (usually 200 heart beats per minute) as the heart rate indicative of stress, from which the user's age has to be subtracted. However, in the case of the invention, such reference values or threshold values take account also of the athletic condition of the user and of the physical heart conditions thereof (tachycardiac, bradycardiac or normal). In this way, reference values are advantageously more corresponding to the user by limiting, if not canceling, the possibility of false alarms.

Preferably, the present method further comprises a step of continuously collecting and analyzing information of one or more user's heart parameters during the usual everyday life of the user.

Therefore, preferably another step follows, still continuously, in which the afore said one or more reference values are determined, and more preferably updated, also on the basis of the afore said continuously-collected information on said one or more user's heart parameters during the usual daily activities of the user.

In this way, reference values are advantageously defined, which are more and more accurate, actual and responsive to the specific user's lifestyle, also depending on the context and the type of activities the user carries out.

This step of continuously collecting and analyzing information of the afore said one or more user's heart parameters during the usual everyday life of the user allows, in fact, obtaining and analyzing specific data per each user, with no interruptions.

Again, determining and updating continuously the afore said reference values, also on the basis of the afore said continuously-collected information of the afore said one or more heart parameters during the usual everyday life of the user that can typically be very different from user to user, allows improving the determination of reference values, as well as the definition of several reference values adapted for specific daily contexts and moments.

Therefore, more the hours of collecting continuously the information relating to user's heart parameters during normal daily activities are, better the definition and the personalization of reference values are.

In this way, in addition to limitation or cancellation of false alarms, at the same time there is an increase of detected cases in which there is a real help need.

According to the invention, it has to be said that the afore said step of continuously collecting and analyzing information of one or more user's heart parameters could concern one or more heart parameters corresponding, altogether or partially, to the afore said one or more measured parameters relating to the user's heart rate to be compared with the afore said reference values relating to the user's heart rate, as well as it could concern information of user's heart parameters different from those measured relating to the user's heart rate, but anyway useful in determining specific reference values relating to the user's heart rate, which can be therefore highly customized.

Again, according to the invention, the present method preferably comprises a first step of acquiring, by recording in at least one first storing system, the afore said information on the user's heart reaction to physical efforts, the afore said information on the level of bradycardia or tachycardia of the user, the afore said continuously-collected information of the afore said one or more user's heart parameters during the usual everyday life of the user, the afore said reference values relating to the user's heart rate and the afore said measured parameters relating to the user's heart rate, more preferably independently one from another.

Preferably, the afore method further comprises a second step of acquiring, by recording in a second storing system, the afore said information on the user's heart reaction to physical efforts, the afore said information on the level of bradycardia or tachycardia of the user, the afore said continuously-collected information of the afore said one or more user's heart parameters during the usual everyday life of the user, the afore said reference values relating to the user's heart rate and the afore said measured parameters relating to the user's heart rate, wherein the afore said information, the afore said values and the afore said measured parameters are communicated and/or transferred from the afore said first storing system to the afore said second storing system.

Preferably, the afore said first storing system or the afore said second storing system is a storing system remote from the afore said user.

Preferably, the afore said method further comprises a step of scheduling the afore said information, the afore said values and the afore said recorded parameters thereby obtaining respective information, values and labeled parameters.

Preferably, the afore said one or more reference values are determined and/or updated on the basis of the afore said information, the afore said values and the afore said labeled parameters.

Preferably, the afore said method might comprise a waiting step, wherein the activation of the afore said alarm, every time one or more of the afore said measured parameters exceeds the afore said reference values, is temporarily suspended, the afore said waiting step being directly controlled by the afore said user.

Still preferably, in the afore said method the afore said alarm is activated every time one or more of the afore said measured parameters exceeds the afore said reference values for a predetermined time interval or the afore said alarm is activated every time one or more of the afore said measured parameters acquires a zero value after the afore said reference values has been exceeded.

Preferably, in the afore said method, the afore said one or more parameters relating to the user's heart rate are measured by at least one heart rate meter and the afore said alarm is controlled by at least one control unit operatively connected to the afore said heart rate meter every time one or more of the afore said measured parameters exceeds the afore said reference values for a predetermined time interval (first time interval), or the afore said alarm is controlled by the afore said at least one control unit or is anyway activated, for example by a remote server, every time one or more of the afore said measured parameters exceeds the afore said reference values and the afore said control unit is not operatively connected to the afore said heart rate meter for a predetermined time interval (second time interval).

Preferably, the afore method comprises a first checking step of ascertaining the activation/deactivation of the afore said control unit, the afore said control unit having at least one first enabled state and a second disabled state, the afore said alarm being activated, possibly by a remote server, every time one or more of the afore said measured parameters exceeds the afore said reference values, the afore said control unit is not operatively connected to the afore said heart rate meter and the afore said control unit is in the afore said enabled state.

According to the invention and what hereinbefore, it follows that in the present method the afore said alarm can be activated also remotely from the afore said user, therefore always automatically, for example by the use of an intended server remote from the user, consequently from the afore said control unit and the afore said heart rate meter.

In practice, in this way the method according to the present invention is provided with an effective protecting or anti-bypass system, which allows the method itself to be effective, hence useful in any circumstance, for example also in case in which the afore said heart rate meter and/or the afore said control unit are tampered.

As a matter of fact the afore said server, operatively connected to the afore said control unit, takes over from the latter in case of need, for example in case of disconnection between the control unit and the heart rate meter, or in case the control unit switches off or breaks down.

Preferably, each of the afore one or more reference values comprises a plurality of reference sub-values relating to the heart rate of the afore said user beyond which the afore said alarm has to be activated, the afore said user being able to selectively select each of the afore said reference sub-values.

Preferably, the afore said plurality of reference sub-values comprises a plurality of different values of the maximum heart rate and/or a plurality of different variations of user's heart rate in a predetermined time interval, the afore said plurality of different values of the maximum heart rate and/or the afore said plurality of variations of heart rate being determined under different use conditions of the afore said method by the afore said user.

Preferably, the afore said method further comprises a second checking step in which the motion state of the afore said user is determined, the afore said reference values and/or the afore said measured parameters being determined and/or updated and respectively selected and/or analyzed on the basis of the afore said motion state of the afore said user.

In view of what above, the objects of the present invention are evidently achieved also by a portable alarm device for a user, and in particular by a device for carrying out the afore described method to which reference is made, comprising:

at least one user heart rate meter;
at least one control unit operatively connected to said meter for detecting the user's heart rate;
at least one memory circuit connected to said control logic unit;
at least one program computer product placed on said memory circuit and capable of being executed by said control unit in order to collect information on the user's heart reaction to physical efforts and on the level of bradycardia or tachycardia of the user, preferably also in order to collect continuously information on one or more user's heart parameters during the usual everyday life of the user, to determine one or more reference values relating to the user's heart rate beyond which said alarm has to be activated, said one or more reference values being determined on the basis of said information on the user's heart reaction to physical efforts and/or the user's level of bradycardia or tachycardia, and preferably also on the basis of the afore said continuously-collected information of the afore said one or more user's heart parameters during the usual everyday life of the user;
alarm means operatively connected to said control unit for the rescue request when the values coming from said heart rate meter are higher than said one or more reference values.

The alarm device further comprises vibration means operatively connected to the control unit to notify the user of the activation of the alarm means.

In particular, advantageously the vibration means allows to reassure the user about the alarm activation without necessarily alerting also the aggressor.

Furthermore, still advantageously, the same vibration means allow the user to deactivate the alarm in case of false detection. Thereby, by programming a predetermined time interval between the vibration and the real alarm activation, false alarms might be substantially canceled.

Again, the alarm device according to the present invention preferably comprises means apt to acquire photos/videos, such as for example a camera, which are removably associated with the afore said control unit or the afore said heart rate meter, more preferably the latter, and operatively connected to the afore said heart rate meter and/or the afore said control unit.

Preferably, the afore said alarm device further comprises an accelerometer associated with the afore said heart rate meter, preferably integrated therewith, and apt to be operatively connected to the afore said heart rate meter and/or the afore said control unit.

BRIEF DESCRIPTION OF THE DRAWINGS

Further characteristics and advantages of the invention will be more evident in view of the detailed description of some preferred embodiments, however not exclusive, of an activation method of an alarm for risk of aggression to a user and a device implementing it, according to the invention, shown by way of non-limiting example with the aid of the attached drawings, in which.

DETAILED DESCRIPTION OF SOME PREFERRED EMBODIMENTS

Figure 1:
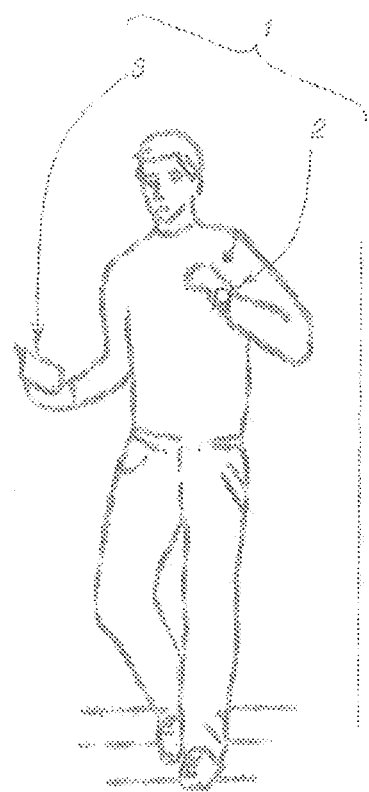
FIG. 1 represents an alarm device according to the invention in an operative moment.
Figure 2:
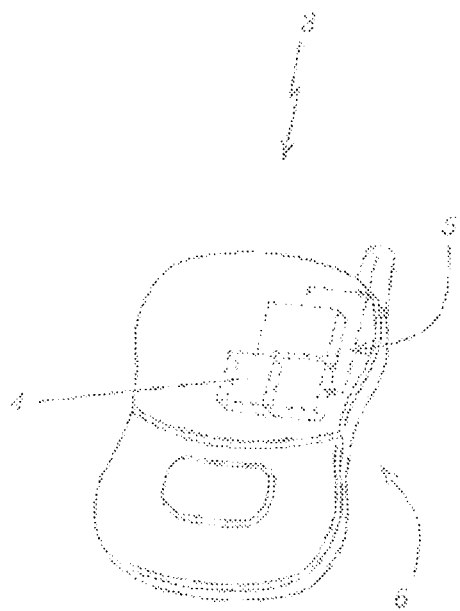
FIGS. 2 and 3 represent details of the device of FIG. 1.
Figure 3:
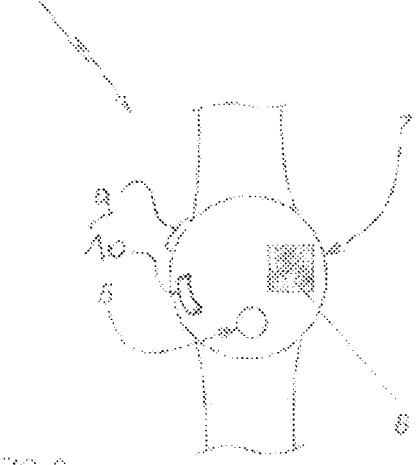

Referring to mentioned figures, a portable alarm device for a user is described, denoted on the whole with the numeral 1. First of all, it comprises a heat rate meter 2. In FIG. 1 such a meter is of wrist type, but this must not be considered limitative to different embodiments.

According to an aspect of the invention the meter comprises, in its turn, an infrared detector with which the physical movement of veins and/or arteries of the wrist has to be measured as a consequence of pulses, and hence the heartbeats.

According to an executive variation not represented in figures, since such detection can be interfered by the sunlight, the meter has shields protecting the detector against sun rays. Signal amplifiers are also present in order to improve the quality of the performed detection.

According to another aspect of the invention, the device 1 comprises a control unit 3 operatively connected to the heart rate meter 2 to detect the user's heart rate. In particular, such a control unit 3 processes received data in order to detect alarm situations. There is also a memory circuit 4 supporting the control unit 3.

In this sense, the device 1 further comprises alarm means 5 operatively connected to the control unit 3 to activate rescue requests in case of danger.

According to the examples of Figures, not to be considered limitative of the invention, the control unit 3 is constituted by a mobile phone 6 operated by an appropriate application having at least one first enabled state and a second disabled state. The heart rate meter 2 is connected to the mobile phone by a Bluetooth wireless connection and the alarm means are a voice and/or date call by the mobile phone to predefined numbers. According to possible executive variations, the alarm means further comprise audio and/or light emitters that are, for example, on the heart rate meter 2.

According to another aspect of the invention, furthermore, the device 1 also comprises vibration means 7 operatively connected to the control unit 3 to notify the user of the activation of the alarm means 5. More in detail, the vibration means are constituted by a vibrator 8 present on the heart rate meter 2 in order to reassure the user about the alarm activation without necessarily alerting the aggressor too.

As mentioned, the same vibration means 7 allow the user to deactivate the alarm in case of false detection. Thereby, by programming a predetermined time interval between the vibration and the real alarm activation, false alarms might be canceled.

Still according to the invention, the present device comprises means apt to acquire photos/videos, denoted on the whole with the numeral 9, such as for example a camera, these means being advantageously integrated in the heart rate meter 2 with the possibility of being integrated in the control unit 3, in every case being operatively connected to the heart rate meter 2 and/or the control unit 3.

Advantageously, the means apt to acquire photos/videos 9 are provided as automatically activated means, being practically means integrating the alarm means 5, and in particular their automatic activation is provided every time one or more predetermined parameters relating to the user's heart rate and measured by the present device exceed/s predetermined reference values relating to the user's heart rate for a predetermined time interval, or their automatic activation is provided every time one or more of these predetermined parameters relating to the user's heart rate and measured by the present device acquire/s a zero value after the same predetermined and measured reference values exceed the predetermined reference values relating to the user's heart rate.

In this case, the present device is effective also in a danger situation in which the removal of the heart rate meter from the user is forced, for example by an aggressor.

According to the invention, the present device further comprises an accelerometer 10 associated with the heart rate meter and apt to be operatively connected to the control unit and/or to the heart rate meter itself.

Advantageously, the accelerometer 10 allows checking the motion state of the user and better determining and/or updating, also instantly, i.e. in the specific moment of the device use, the reference value/s relating to the user's heart rate, as well as it allows selecting and/or analyzing at best the measured parameters relating to the user's heart rate.

Still advantageously, the accelerometer 10 allows determining several reference values for the same parameter of user's heart rate, then multi-thresholds for a predetermined parameter of user's heart rate, the multi-thresholds being varied depending on the specific current user's activity that could change, for example, during the same day depending on the different activities the user carries out.

In addition a manually-operated control is provided, advantageously housed in the heart rate meter, however the possibility of providing for its driving by the control unit is not excluded, which allows temporarily suspending the alarm activation when the afore said one or more predetermined parameters relating to the user's heart rate and measured by the present device, exceeds the predetermined reference values relating to the user's heart rate.

In this case, the user can directly avoid a false positive by driving the afore said control before the alarm is activated, for example in case of aggression initially suspected and then warded off.

For what above, it is evident that a fundamental element of the invention is the application on the mobile phone 6, i.e. a program computer product resident in the memory circuit 4 and capable of being executed by the control unit 3 so that to conveniently control all the device 1.

More in detail, such a program computer product allows the control unit 3, from an operative point of view, to control the execution of some steps.

Firstly, there are initial steps of collecting information, i.e. self-learning steps for customize the device 1 with personal data of the user using it.

In this sense, there is a first step of collecting information on the user's heart reaction to physical efforts. More in detail, in this step the heart rate meter 2 detects, with the control of the unit 3, the user's heart rate during a predefined effort, such as a walk at a cracking pace lasting six minutes. Obviously, the effort type and the duration of such an effort are elements not binding on the present invention, as they are only a possible effort example. Also the type of detected parameter is only one of the possible heart parameters to be detected for the invention purposes.

Afterwards, there is a second step of collecting information on the user's level of bradycardia or tachycardia. In particular for a predefined period that, in this embodiment, is of twenty-four hours but not constituting a limitation of the present invention, the user's heart rate is detected to determine heart rate parameters such as, for example, the normal heart rate of the user in order to determine if the latter is in the norm or suffers from bradycardia or tachycardia.

Lastly, there is a third step of continuously collecting information of one or more heart rate parameters of the user during the usual everyday life of the user, which can typically be very different from user to user, this step being apt to determine information on heart parameters of the user during different daily contexts and moments. In particular, examples non-limiting the present invention, during work activities, displacements, moments of relaxation, sleep or sport activities.

It is understood that such a step of continuously collecting information of one or more user's heart parameters may advantageously coincide with the period of active use of the present device, then with the active use of the present method.

All these detections are stored in the memory circuit 4 and, subsequently, processed so that a threshold heart rate and a variation of the threshold heart rate are calculated, i.e. reference values relating to the heart rate and the variation of the heart rate of the user, beyond which the alarm has to be activated.

As mentioned above, in fact, these thresholds are reached or exceeded only in high stress and anxiety situations typically due to mugging or similar events.

As a matter of fact, it is known that such reference values, therefore the threshold values, are surely higher than heart rate values, or variations of heart rate, due to physical efforts or other situations normally happening during the day, the whole being obviously compared to the effective conditions of the user.

Typically, these reference values can be determined by referring to a reference value, as the heart rate indicative of stress, that in the medical field is typically, but not necessarily, set to 200 heart beats per minute. From such a value the number of heart beats corresponding to the user's age has to be subtracted, as it is known that when the age increases, not only the number of user's heart beats per minute decreases, but also the maximum number of heart beats reached in case of stress the user can withstand. Obviously, also these values are to be considered as non-limitative of the invention.

In any case, reference values take into account also of the athletic condition of the user and the heart physical conditions thereof (tachycardiac, bradycardiac or normal), as well as of the user's lifestyle, i.e. these thresholds are compared to the effective user's conditions (personal physical condition, outer ambient condition, type of real activities of the user) so that to limit, if not to cancel, the possibility of false alarms and/or the failed start in case of real needs.

In particular, an athletically trained user has a smaller number of heart beats at rest and a smaller range of heart rate in case of effort and in case of high stressful situations, such as an aggression. In this sense, detected values are processed so that to decrease the reference heart rate/s beyond which the alarm is set off. A non-limitative example of the invention is to force as the threshold heart rate, possibly as the initial threshold heart rate depending on which subsequent calculations will be carried out, based on data relating to the bradycardia or tachycardia level as well as the user's lifestyle, an average rate between the previously mentioned medical reference value subtracted of the patient (user) age and the maximum heart rate reported during the predefined effort.

For what concerns the user's heart conditions detected during the second step of collecting information, as mentioned they allow determining if the user is bradycardiac, tachycardiac, or normal. As known, a user is bradycardiac if he/she has, at rest, a number of heart beats per minute comprised between 40 and 60, whereas is tachycardiac if the number of heart beats is higher than 100. In these cases, evidently the threshold beyond which the alarm has to be activated must be changed consequently. In particular, collected data are processed so that to obtain a tachycardia or bradycardia index, i.e. an index proportional to the deviation of heart rate from limit values, for example, of 60 heart beats per minute or 100 heart beats per minute.

In case of bradycardia the alarm threshold has to be decreased of a value proportional to such an index, whereas in case of tachycardia such a threshold has to be increased of a value proportional to the afore said corresponding index. By doing so the threshold of heart rate, beyond which the alarm has to be set off, is adapted to effective conditions of the user and allows limiting the possibility of false alarms.

Lastly, for what concerns the user's lifestyle, therefore the usual everyday life, continuously-registered information on heart parameters allow a better definition of levels of physical and emotional efforts to which the user is daily subjected to, as the method use hours, therefore the use hours of the present device, increase.

Advantageously such levels, with the information collected in the afore said steps, allow the definition of multiple reference values specific for different contexts and moments of the day. By doing so the thresholds of heart rate, beyond which the alarm has to be set off, are adapted not only as a function of the physical or emotional effort but also as a function of the user's lifestyle, habit and various moments in which he/she decides to activate the present device.

However, since there are some situations in which such a threshold can not be reached despite the aggression, the device 1 considers another parameter, which is the variation of the heart rate in the short term (for example a few seconds). In case of stress, as a matter of fact, such a variation is higher than the variations that could happen, in the same time interval (for example two seconds), in case of physical effort or similar. Therefore, controlling also such a parameter advantageously allows limiting, if not canceling, the possibility the alarm does not set off, despite the aggression.

Therefore, operatively, after the initial steps of self-learning and processing for determining the thresholds of monitored heart parameters, the device 1 starts the active step, i.e. it is activated a step of measuring these parameters and possibly activating the alarms every time one or more of said measured parameters exceed the reference values.

Furthermore, advantageously, according to what above, in such an active step the device keeps collecting information on user's heart parameters and analyzing the collected information (data) thereby increasing, during time, its own user's knowledge and achieving the possibility of defining reference parameters which are more and more specific and suitable for the same user.

In particular, when the set thresholds are exceeded, the control unit 3 initially drives the activation of the vibration means 7 for a predetermined period that could be, as a non-limitative example, 30 seconds during which the user can deactivate the alarm as it is a false positive. Should it not be the case, the alarm is activated and the rescue request is sent.

According to embodiment variations of the inventions able to further decrease false positives as well as not-detected danger and aggression situations, the present method comprises additional steps between which an improvement of the auto-learning steps, therefore of the steps of collecting information and processing information, in particular in order to achieve a high customization of the present device both depending on the specific user, and depending on the specific time interval or employment condition in which the device is used by the afore said specific user.

According to what above, therefore the definition of multi-thresholds for an unique parameter relating to the user's heart rate, in which each multi-threshold for the given parameter relating to the user's rate corresponds to a different user's activity, and the registration of values of measured parameters and/or information collected by the device, both in the self-learning step and in the active using step, in at least one storing system, possibly a storing system remote from the device, therefore remote from the user, with exchange of data/information between the device and the storing system, possibly through a remote server, i.e. a server outside of the present device, are provided.

Therefore, preferably, the present method further comprises a first step of acquiring, by recording in at least one first storing system, the information on the user's heart reaction to physical efforts, the information on the level of bradycardia or tachycardia of the user, the continuously-collected information of one or more user's heart parameters during the usual everyday life of the user, the reference values relating to the user's heart rate and the measured parameters relating to the user's heart rate, possibly independently from one another, and more preferably it comprises a second step of acquiring, by recording in a second storing system, the information on the user's heart reaction to physical efforts, the information on the level of bradycardia or tachycardia of the user, the continuously-collected information of one or more user's heart parameters during the usual everyday life of the user, the reference values relating to the user's heart rate and the measured parameters relating to the user's heart rate, wherein the afore said information, the afore said values and the afore said measured parameters are communicated and/or transferred from the first storing system to the second storing system, and wherein the second storing system is advantageously a storing system remote from the user.

Still more preferably, the present method further comprises a step of scheduling the afore said information, the afore said values and the afore said recorded parameters thereby obtaining respective information, values and labeled parameters, depending on which the afore said one or more reference values are determined and/or updated.

Still preferably, the present method comprises a waiting step wherein the activation of the alarm, every time one or more of the measured parameters exceeds the reference values, is temporarily suspended, and wherein the waiting step is directly controlled by the user.

According to the invention, the waiting step has to be started before the effective alarm activation, i.e. before the rescue request is sent.

As mentioned before, in order to reduce or canceling false positives, in the present method the alarm is preferably activated every time one or more of the afore said measure parameters relating to the user's heart rate exceeds the afore said reference values for a predetermined time interval and, according to the invention, the alarm is additionally activated every time one or more of the afore said measured parameters relating to the user's heart rate acquires a zero value after the afore said reference values has been exceeded.

Zero value can be determined, for example, due to detachment of the heart rate meter from the user, for example after a fight against an aggressor, or death of the user after an aggression.

In these cases, the alarm request is anyway sent if the afore said one or more measured parameters exceeds the afore said reference values also for a time interval shorter than the predetermined one, i.e. shorter than a first time interval.

According to what above, therefore, the afore said one or more parameters relating to the user's heart rate are measured by the heart rate meter and the alarm is controlled by the control unit operatively connected to the heart rate meter every time one or more of the afore said measured parameters exceeds the afore said reference values for the first predetermined time interval, or according to an additional aspect of the invention, the alarm is controlled by the afore said at least one control unit or it is anyway activated, for example by a remote server connected to the heart rate meter and/or the control unit, every time one or more of the afore said measured parameters exceeds the afore said reference values and the control unit is not operatively connected to the heart rate meter for a second predetermined time interval, for example a second time interval shorter than the afore said first time interval.

Also in this case, the alarm request is anyway sent if the afore said one or more measured parameters exceeds the afore said reference values for a time interval shorter than the afore said first predetermined time interval, for example because of an undesirable disconnection between the control unit and the heart rate meter caused by an aggressor.

Again, the present method preferably comprises also a first checking step of ascertaining the activation/deactivation of the control unit, i.e. if it is in the afore said enabled state or in the afore said disabled state, and according to an additional aspect of the invention, the alarm is activated every time one or more of the afore said measured parameters exceeds the afore said reference values, the afore said control unit is not operatively connected to the afore said heart rate meter for a predetermined time interval and the afore said control unit is in the afore said enabled state.

In conclusion, the enabled state of the control unit is represented by a so-called running condition of the afore said application, i.e. the program computer product, whereas a disabled state is represented by a condition in which the application, therefore the program computer product, is shut down.

Advantageously the switching of the application, i.e. the control unit, from the running state to the shut down state, and vice versa, can be subordinate to the use of a security code.

On the other hand, a condition in which a heart rate meter and the control unit are operatively not connected could happen, for example, when the control unit and the heart rate meter are excessively distant one from another for their interaction, or when the control unit is switched off.

As evident from what mentioned above, the control unit cannot be operatively connected to the heart rate meter because the first is switched off, but it can be in the enabled state.

From what above, also in the latter case just now set forth, the alarm is advantageously activated by a remote server connected to the heart rate meter and/or the control unit.

Concerning the afore said multi-thresholds, according to what mentioned above, it has to be said that in the present method each of the afore said one or more reference values preferably comprises a plurality of reference sub-values relating to the user's heart rate beyond which the alarm has to be activated, in which each of the reference sub-values is selectively selectable by the user.

Preferably, the plurality of reference sub-values comprises a plurality of different values of the maximum heart rate and/or a plurality of different variations of user's heart rate in a predetermined time interval, in which the plurality of different values of the maximum heart rate and/or the plurality of variations of heart rate are determined under different use conditions of the present method for the same user.

Preferably, the afore method further comprises a second checking step in which the motion state of the user is determined, the afore said reference values and/or the afore said measured parameters being determined and/or updated and respectively selected and/or analyzed on the basis of the motion state of the user.

In view of what above, it is understood that the activation method of an alarm for risk of aggression to a user and the alarm device implementing it, overcome the drawbacks of the known art by being automatically activated and allowing, with respect to the known devices, limiting, if not canceling, false alarms.

In addition, they allow also limiting, if not canceling, the alarm situations that are not reported because not detected.

In practice, the present invention allows activating an alarm in any aggression circumstance, or risk of aggression, thereby being able to distinguish between situations in which, in a manner of speaking, the user himself determines particular events, and situations in which the particular event is determined by an aggression to the user.

The activation method of an alarm for risk of aggression of the invention and the alarm device implementing it, are susceptible to a number of modifications and variations, all falling in the inventive conception stated in the attached claims. All details could be replaced by other technically equivalent elements, and materials could be different depending on needs, without departing from the scope of the invention.

Also if the activation method of an alarm for risk of aggression of the invention and the alarm device implementing it have been described particularly referring to attached figures, the reference numerals used in description and claims are used for increasing the ingenuity of the invention and are not limitative of the claimed scope of protection.

The invention claimed is:
1. An activation method of an alarm for risk of aggression to a user comprising:
  collecting information on the user's heart reaction to physical efforts;

collecting information on the level of bradycardia or tachycardia of the user;

determining one or more reference values relating to the user's heart rate beyond which said alarm has to be activated, said one or more reference values being determined on the basis of said information on the user's heart reaction to physical efforts and/or the bradycardia or tachycardia level of the user;

measuring one or more parameters relating to the user's heart rate wherein said one or more parameters relating to the user's heart rate is/are measured by at least one heart rate meter; and activating said alarm, wherein said alarm is controlled by at least one control unit, every time one or more of said measured parameters exceeds said reference values and said control unit is not operatively connected to said heart rate meter for a second predetermined time interval after said one or more measured parameters exceed said reference values.

2. The method of claim 1, wherein said one or more reference values comprise a value of the maximum heart rate, said measured parameters comprising the user's heart rate.

3. The method of claim 2, wherein said value of the maximum heart rate is calculated by subtracting the user's age from a predetermined medical value of heart rate.

4. The method of claim 2, wherein said value of the maximum heart rate is calculated by subtracting a first correction value of the heart rate from a predetermined medical value of heart rate, said first correction value being proportional to an index of bradycardia.

5. The method of claim 2, wherein said value of the maximum heart rate is calculated by adding a second correction value of the heart rate to a predetermined medical value of heart rate, said second correction value being proportional to an index of tachycardia.

6. The method of claim 1, wherein said reference values comprise the variation of heart rate in a predetermined time interval, and said measured parameters comprise the variation of user's heart rate in said predetermined time interval.

7. The method of claim 1, wherein said step of collecting information on the user's heart reaction to physical efforts occurs by measuring the user's heart rate at regular time intervals during a walk at a cracking pace for a predetermined duration.

8. The method of claim 1, wherein said step of collecting information on the level of bradycardia or tachycardia of the user occurs by measuring the user's heart rate at regular time intervals for a predetermined period of life of the user.

9. The method of claim 1, wherein further comprising a step of continuously collecting and analyzing information of one or more user's heart parameters during the usual everyday life of the user.

10. The method of claim 9, wherein said one or more reference values are continuously determined and/or updated on the basis of said continuously-collected information of said one or more user's heart parameters.

11. The method of claim 1, further comprising a first step of acquiring, by recording in at least one first storing system, said information on the user's heart reaction to physical efforts, said information on the level of bradycardia or tachycardia of the user, said continuously-collected information of said one or more user's heart parameters during the usual everyday life of the user, said reference values relating to the user's heart rate and said measured parameters relating to the user's heart rate.

12. The method of claim 11, further comprising a second step of acquiring, by recording in a second storing system, said information on the user's heart reaction to physical efforts, said information on the level of bradycardia or tachycardia of the user, said continuously-collected information of said one or more user's heart parameters during the usual everyday life of the user, said reference values relating to the user's heart rate and said measured parameters relating to the user's heart rate, wherein said information, said values and said measured parameters are communicated and/or transferred from said at least one first storing system to said second storing system.

13. The method of claim 11, wherein said first storing system is a storing system remote from said user.

14. The method of claim 12, wherein said second storing system is a storing system remote from said user.

15. The method of claim 11, further comprising a step of scheduling said information, said values and said recorded parameters thereby obtaining respective information, values and labeled parameters.

16. The method of claim 15, wherein said one or more reference values are determined and/or updated on the basis of said information, said values and said labeled parameters.

17. The method of claim 1, further comprising a waiting step wherein the activation of said alarm, every time one or more of said measured parameters exceeds said reference values, is temporarily suspended, said waiting step being directly controlled by said user.

18. The method of claim 1, wherein said alarm is activated every time one or more of said measured parameters exceeds said reference values for a predetermined time interval or wherein said alarm is activated every time one or more of said measured parameters acquires a zero value after said reference values has been exceeded.

19. The method of claim 1, said method further comprising a first checking step of ascertaining the activation/deactivation of said control unit, said control unit having at least one first enabled state and a second disabled state, said alarm being activated every time one or more of said measured parameters exceeds said reference values, said control unit is not operatively connected to said heart rate meter after said one or more measured parameters exceed said reference values and said control unit is in said enabled state.

20. The method of claim 1, wherein each of said one or more reference values comprises a plurality of reference sub-values relating to the user's heart rate beyond which said alarm has to be activated, said user being able to selectively select each of said reference sub-values.

21. The method of claim 20, wherein said plurality of reference sub-values comprises a plurality of different values of the maximum heart rate and/or a plurality of different variations of user's heart rate in a predetermined time interval, said plurality of different values of the maximum heart rate and/or said plurality of variations of heart rate being determined under different use conditions of said method by said user.

22. The method of claim 1, further comprising a second checking step in which the motion state of said user is determined, said reference values and/or said measured parameters being determined and/or updated and respectively selected and/or analyzed, preferably instantaneously, on the basis of said motion state of said user.

23. A portable alarm device for a user comprising:
at least one user heart rate meter;
at least one control unit operatively connected to said heart rate meter for detecting the user's heart rate;

at least one memory circuit connected to said control unit;

at least one program computer product placed on said memory circuit and capable of being executed by said control unit in order to collect information on the user's heart reaction to physical efforts and on the level of bradycardia or tachycardia of the user and also in order to collect continuously information on one or more user's heart parameters during the usual everyday life of the user, to determine one or more reference values relating to the user's heart rate beyond which said alarm has to be activated, said one or more reference values being determined on the basis of said information on the user's heart reaction to physical efforts and/or the user's level of bradycardia or tachycardia, and also on the basis of said continuously-collected information of said one or more user's heart parameters; and alarm means for the rescue request when the values coming from said heart rate meter are higher than said one or more reference values, wherein said alarm means are controlled by said at least one control unit and activated every time said control unit is not operatively connected to said heart rate meter for a second predetermined time interval after said one or more measured parameters exceed said reference values.

24. Portable alarm device according to claim 23, further comprising vibration means operatively connected to said control unit to notify the user of the activation of said alarm means.

25. Portable alarm device according to claim 23, further comprising means apt to acquire photos/videos which are removably associated with said heart rate meter and apt to be operatively connected to said heart rate meter and/or said control unit.

26. Portable alarm device according to claim 23, further comprising an accelerometer associated with said heart rate meter and apt to be operatively connected to said heart rate meter and/or said control unit.

* * * * *